(12) United States Patent
Bernstein et al.

(10) Patent No.: US 6,356,774 B1
(45) Date of Patent: Mar. 12, 2002

(54) OXIMETER SENSOR WITH ENCODED TEMPERATURE CHARACTERISTIC

(75) Inventors: Michael J. Bernstein, San Ramon; Michael E. Fein, Mt. View; William L. Shea, Livermore; Willem A. Crone, Palermo; Paul D. Mannheimer, Danville; Bradford Chew, San Ramon; Adnan Merchant, Fremont, all of CA (US)

(73) Assignee: Mallinckrodt, Inc., Hazelwood, MO (US)

(*) Notice: Subject to any disclaimer, the term of this patent is extended or adjusted under 35 U.S.C. 154(b) by 0 days.

(21) Appl. No.: 09/407,469

(22) Filed: Sep. 28, 1999

Related U.S. Application Data
(60) Provisional application No. 60/102,256, filed on Sep. 29, 1998.

(51) Int. Cl.$^7$ .................................................. A61B 5/00
(52) U.S. Cl. ...................... 600/323; 600/322; 600/331
(58) Field of Search ................................. 600/309–312, 600/316–317, 322–329, 331–332, 334, 336, 364; 250/205, 238; 356/39–42

(56) References Cited

U.S. PATENT DOCUMENTS

| | | | |
|---|---|---|---|
| 3,705,316 A | * 12/1972 | Burrous et al. ............. 307/311 |
| 3,720,199 A | 3/1973 | Rishton et al. |
| 3,790,910 A | 2/1974 | McCormack |
| 4,228,805 A | * 10/1980 | Rosen et al. ................ 600/504 |
| 4,303,984 A | 12/1981 | Houvig ........................ 364/571 |
| 4,529,949 A | * 7/1985 | De Wit et al. ............... 330/289 |
| 4,621,643 A | 11/1986 | New, Jr. et al. |
| 4,684,245 A | 8/1987 | Goldring ...................... 356/41 |
| 4,700,057 A | * 10/1987 | Sakai .......................... 250/205 |
| 4,700,708 A | 10/1987 | New, Jr. et al. |
| 4,869,253 A | * 9/1989 | Craig et al. ................. 600/323 |
| 4,913,150 A | 4/1990 | Cheung et al. |
| 4,942,877 A | 7/1990 | Sakai et al. |
| 5,007,423 A | * 4/1991 | Branstetter et al. ......... 600/334 |
| 4,446,715 A | 9/1991 | Bailey ............................. 73/1 |
| 5,106,360 A | * 4/1992 | Ishiwara et al. ............... 600/2 |
| 5,246,003 A | 9/1993 | DeLonzor |
| 5,259,381 A | * 11/1993 | Cheung et al. ............. 600/323 |
| 5,401,099 A | * 3/1995 | Nishizawa et al. .......... 374/178 |
| 5,477,853 A | * 12/1995 | Farkas et al ................ 600/310 |
| 5,529,755 A | 6/1996 | Higashio et al. ......... 422/82.09 |
| 5,651,780 A | 7/1997 | Jackson et al. ................. 606/1 |
| 5,758,644 A | * 6/1998 | Diab et al ................... 600/323 |
| 5,766,127 A | * 6/1998 | Pologe et al. ............... 600/310 |
| 5,769,784 A | * 6/1998 | Barnett et al. .............. 600/300 |
| 5,779,630 A | * 7/1998 | Fein et al. ................... 600/323 |
| 5,792,053 A | 8/1998 | Skladnev et al. ........... 600/407 |
| 6,026,323 A | * 2/2000 | Skladnev et al. ........... 600/547 |

* cited by examiner

*Primary Examiner*—Eric F. Winakur
*Assistant Examiner*—Matthew Kremer
(74) *Attorney, Agent, or Firm*—Townsend and Townsend and Crew LLP

(57) ABSTRACT

A method for operating an oximeter sensor, and corresponding apparatus, which includes an encoded temperature characteristic of a light emitter in the sensor. The encoded temperature characteristic is read, and is used to modify a drive of the light emitter in the sensor. This enables a light emitter to be operated at its maximum allowable intensity to maximize a signal to noise ratio, without burning a patient, in accordance with the particular characteristics of that light emitter.

23 Claims, 8 Drawing Sheets

OXIMETER SENSOR WITH ENCODED TEMPERATURE CHARACTERISTIC

CROSS-REFERENCE TO RELATED APPLICATIONS

This application claims priority from U.S. Provisional Application Serial No. 60/102,256, filed Sep. 29, 1998 which is incorporated herein by reference in its entirety for all purposes.

BACKGROUND OF THE INVENTION

The present invention relates to optical medical sensors, especially oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

The intensity of the light emitters in the sensor, typically LEDs, can be controlled by controlling their drive current. Generally, it is advantageous to have a higher intensity level to increase the signal to noise ratio of the signal received at the detector. The amount of drive can vary depending upon the characteristics of the particular LEDs and detector. Thus, some oximeters will vary the drive current to the LEDs in accordance with the signal received from the detectors until an optimum level has been obtained. In particular, the drive current may vary between a red and an infrared LED, with different drive levels required for the different types of LEDs to ensure that both fall within the range of an analog-to-digital converter connected to the amplified detector signal. One limitation on the amount of drive current is that too high a current could cause the LEDs to emit sufficient heat to burn the patient. Accordingly, a maximum current allowable is often imposed, and is chosen to be conservative taking into consideration the variations in LED performance from LED to LED, and also taking into consideration the different heat-dissipating properties of the tissue of different patients to whom the sensors may be connected.

An example of an encoding mechanism not related to controlling drive current is shown in U.S. Pat. No. 4,700,708. This relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs actually manufactured can vary, a resistor is placed in the sensor with the value of the resistor corresponding to the actual wavelength of at least one of the LEDs. When the instrument is turned on, it first applies a current to the coding resistor and measures the voltage across the resistor to determine the value of the resistor and thus the value of the wavelength of the LED in the probe.

U.S. Pat. No. 4,913,150 recognizes that the coded value of the wavelength of the red LED provided by a coding resistor may be inaccurate, since the actual wavelength can vary with temperature. Accordingly, this patent teaches including a temperature sensor in the oximeter sensor to measure the actual temperature. With the actual temperature, and the coded wavelength value, a look-up table can be consulted to determine the actual LED wavelength for that temperature.

Another method of storing coded information regarding the wavelength characteristics of the LEDs is shown in U.S. Pat. No. 4,942,877. This patent discloses using an EPROM memory on the sensor to store digital information, which can be provided in parallel or serially from the sensor probe to a remote oximeter.

Other examples of coding sensor characteristics exist in other areas. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another sensor with digital characterization information stored in a PROM, which is read serially using a shift register. U.S. Pat. No. 5,651,780 shows a catheter having means for generating a uniquely coded identification signal. This signal may contain a variety of information, including the presence of a temperature sensor or thermistor and its associated resistance calibration, and the catheter product number.

Typically, the coding element is mounted in the sensor itself. For instance, U.S. Pat. No. 4,621,643 shows the coding resistor mounted in the sensor element itself. In addition, U.S. Pat. No. 5,246,003 shows the coding resistor being formed with a printed conductive material on the sensor itself.

In some devices, an electrical connector coupled by a cable to a device attached to a patient may include a coding element. For example, U.S. Pat. No. 3,720,199 shows an intra-aortic balloon catheter with a connector between the catheter and the console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

SUMMARY OF THE INVENTION

The present invention provides a method for operating an oximeter sensor, and corresponding apparatus, which includes in the sensor, or in a sensor attachment (e.g., connecting cable or plug), an element such as a light emitter, having a temperature-dependent electrical characteristic. The temperature dependence of the electrical characteristic is encoded in a component of the sensor assembly. The encoded temperature characteristic is read, and is used to modify the driving of the light emitter in the sensor. This enables a light emitter to be operated at its maximum allowable intensity to maximize the signal to noise ratio, without burning a patient, in accordance with the particular characteristics of that light emitter.

In one embodiment, the temperature at the patient's skin can be estimated from the junction temperature of an LED contained in a pulse oximeter sensor. The junction temperature can be measured by driving the junction with a fixed current and measuring the corresponding forward voltage drop. The peak skin temperature under the LED can be estimated computationally from the junction temperature, the power dissipated in the sensor LEDs, and the effective thermal conductivities of the sensor body and of the patient.

In another embodiment of the invention, the junction temperature of an LED incorporated in a medical optical sensor may be determined in order to compute the shift in principal wavelength of the LED. This allows a more accurate computation of the shift than has previously been possible in LED-based medical optical sensors. The wavelength-shift information in turn may be used to select or compute a calibration curve for determining arterial oxygen saturation for the sensor with higher accuracy than would otherwise have been possible.

In another aspect of the present invention, the voltage across a sensor element for given drive current is measured, and compared to a calibration value. A variance, especially one indicating a higher resistance, can indicate worn or damaged connections, while a lower resistance could indicate a short-circuit condition. Thus, an error signal indicating a defective sensor can be automatically produced.

In still another aspect of the invention, the apparent forward voltage across an element (e.g., an LED) in the sensor is measured at two different currents. A dynamic resistance value of the element is provided by one of several means, and is used in combination with the two measured forward voltages to determine the series resistance between the instrument and the element. This permits the actual forward voltage across the element to be determined more accurately, with a resulting enhancement of temperature measurement accuracy.

For further understanding of the nature and advantages of the invention, reference should be made to the following description taken in conjunction with the accompanying drawings.

DETAILED DESCRIPTION OF THE INVENTION

At any given current, the forward voltage across a semiconductor diode usually will decrease with increasing temperature. LEDs are examples of semiconductor diodes having this property. It is well known to measure the temperature of a semiconductor diode junction by measuring the forward voltage across the junction while a small test current is applied. The test current must be large enough to overcome surface leakage effects but small enough not to cause significant self-heating. A typical test current used for LEDs is 1 mA. A common application of such methods has been to evaluate the thermal conductivity of the die attachment by which a semiconductor device is mounted to its substrate. We have recognized that these known methods can be applied to temperature monitoring in medical optical devices, which permits the addition of a temperature sensing function to a medical optical sensor at very low incremental cost of materials, at the expense of an additional calibration process during device manufacture.

Figure 1:
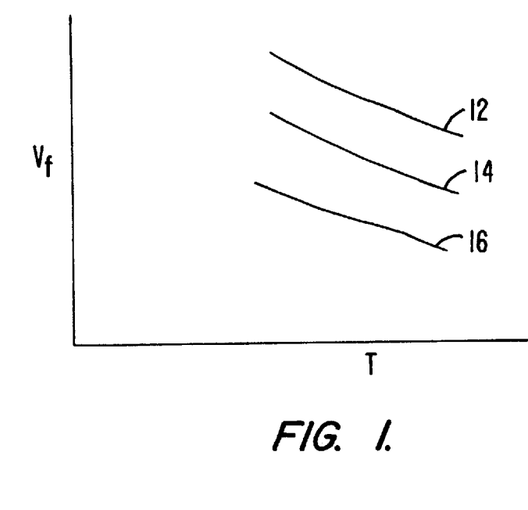
FIG. 1 is a graph illustrating the calibration curves for the forward voltage of an LED versus temperature.

One characteristic of light emitters, such as LEDs, is that they vary from device to device, due to process variations in the manufacturing of the LEDs. FIG. 1 is a graph illustrating three examples of curves for particular LEDs showing a plot of their forward voltage ($V_f$) versus temperature (T), at a particular test current such as 1 mA. The three curves are identified as 12, 14, and 16. As can be seen, each curve approximates a straight line. A typical slope may be in the range of −2 mV/° C.

By driving the LEDs in the factory with a fixed test current while exposing them to several different controlled temperatures, the appropriate curve from FIG. 1 corresponding to a particular LED can be identified. Once identified, these various curves can be categorized into bins of curves of approximately the same values. An encoding resistor, or other encoding means, can then be placed in each sensor to identify the correct bin or curve for that particular LED. It is possible to calibrate both red and infrared LEDs of a sensor in this way, and to provide a separate encoding resistor for each. It is also possible to encode the bins of both red and IR LEDs with a single resistor, if available resistors and readout instrumentation permit a sufficient number of distinguishable resistance ranges. In certain sensor structures, it is known by design that the temperatures of both red and IR LEDs will always be sufficiently similar to permit only one of them to be measured; in this case only the LED whose junction temperature is to be measured need be calibrated and assigned to a bin. The calibration curve of an LED can be approximated by a straight line with of the formula $T=aV_f+b$, with a and b being stored in a table. Equivalently, the calibration curve may be approximated by a straight line of the formula $V_f=V_{f0}+k(T-T_0)$, where k is a slope and $V_{f0}$ is the voltage at a particular temperature $T_0$, with k and $V_{f0}$ being stored in a table. Table 1 is an example of such a table.

TABLE 1

| Bin number | Resistance range, ohms | Slope, mV/° C. | $V_f$ at 40° C. |
|---|---|---|---|
| 1 | 100 to 199.5 | −1.90 to −2.00 | 1.5000 to 1.5019 |
| 2 | 200 to 299.5 | −1.90 to −2.00 | 1.5020 to 1.5029 |
| 3 | 300 to 399.5 | −1.90 to −2.00 | 1.5030 to 1.5039 |
| 4 | 400 to 499.5 | −2.01 to −2.10 | 1.5000 to 1.5019 |
| 5 | 500 to 599.5 | −2.01 to −2.10 | 1.5020 to 1.5029 |
| 6 | 600 to 699.5 | −2.01 to −2.10 | 1.5030 to 1.5039 |

Table 1 is constructed on the assumption that all LEDs likely to be encountered can be sorted into one of six bins, and that an oximeter can discover the calibration curve associated with each LED by determining which of six resistance codes has been incorporated in the sensor. In addition to the selection of an encoding resistor value, many other forms of encoding are known, some of which have been referenced herein, and the use of any of them is contemplated within the scope of the present invention. We also include, within the meaning of "encoding", the storage (in a digital device incorporated in the sensor assembly) of coefficients in a formula which represent a calibration curve. For example, for a particular LED included in Bin 3 above, the stored numbers might be a slope of −1.930 mV/° C. and an intercept of 1.5035 V. Also included within the meaning of "encoding" is the storage (in a digital device incorporated in the sensor assembly) of a table of corresponding voltages and temperatures for a particular LED. Table 2 is an example of such a table. While the temperature values at which voltages are tabulated in Table 2 are relatively widely spaced, the voltages corresponding to other temperatures may be determined using own numerical methods of interpolation and extrapolation.

TABLE 2

| Temperature, ° C. | $V_f$, volts |
|---|---|
| 0 | 1.5835 |
| 10 | 1.5635 |
| 20 | 1.5435 |
| 30 | 1.5235 |
| 40 | 1.5035 |
| 50 | 1.4835 |
| 60 | 1.4635 |
| 70 | 1.4435 |
| 80 | 1.4235 |

Figure 4A:
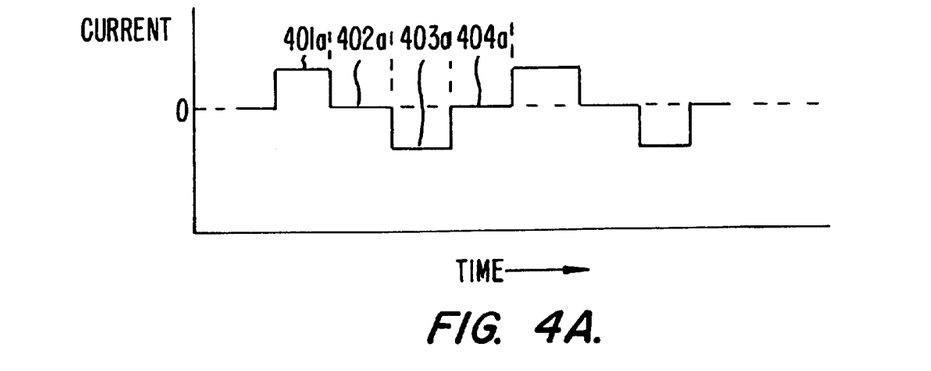
FIGS. 4A–4C are diagrams illustrating exemplary waveforms for use in driving an oximeter's LEDs and determining the junction temperature of at least one of them.
Figure 4B:
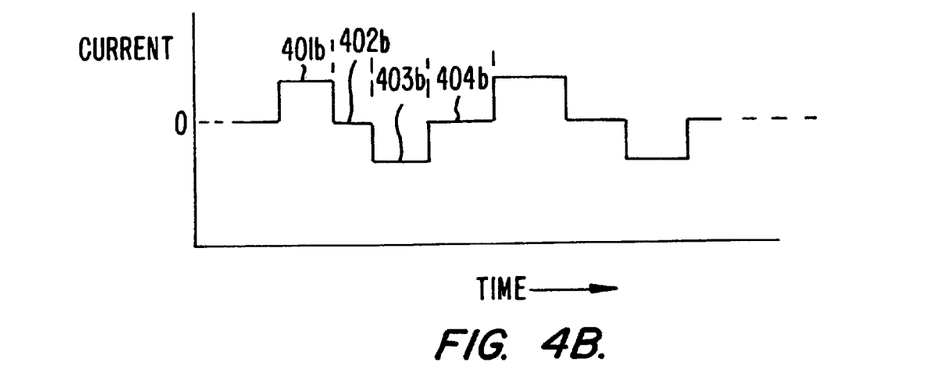
Figure 4C:
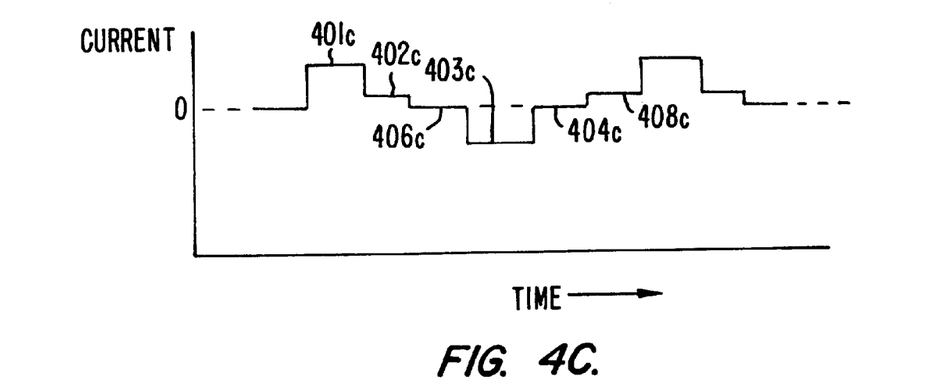

Given the factory calibration, and a means of communicating that calibration to the oximeter instrument, it is possible for the oximeter to measure $V_f$ and from that to determine junction temperature. Determination of $V_f$ does require that special provision be made for switching the oximeter's LEDs between normal operating currents and the low test current used for temperature measurement. Typically, a pulse oximeter will drive its LEDs at currents much exceeding the test current at which factory calibration is performed. The reason for making the calibration current low compared to typical operating currents is that the operating currents may be high enough to cause significant self-heating of the LED. At such currents, it is not practical to determine the actual temperature of the LED junction during calibration simply by measuring the temperature of a substrate to which the LED is clamped. The added difficulty of determining true junction temperature under such conditions would make it difficult to establish an economical high-volume calibration process. This leads to the practical decision to perform temperature calibration at a low current, such as 1 mA, and to the necessity for the oximeter to switch between a driving current used for oximetry and a low test current used for temperature measurement. FIG. 4 shows examples of waveforms that might be applied to the LEDs, to permit both oximetry and temperature determination.

FIG. 4a shows, for comparison, a prior-art waveform that is often used for driving a back-to-back pair of LEDs. During period 401a, the red LED is on. During period 403a, the IR LED is on. During periods 402a and 404a, neither LED is on. The oximeter can use sample detector outputs gathered during periods 402a and 404a to establish references for optical and electrical background radiation, to be subtracted from the signals collected during periods 401a and 403a.

FIG. 4b shows a modified waveform which may be used when temperature sensing is desired. Now, during the "dark" periods 402b and 404b, there is actually a small test current flowing (this current may be 1 mA), so that $V_f$ can be measured. If optical signals during this period are used as a reference for comparison of signals collected during the "bright" periods, there will be a slight diminution of the net detected signal, as if a small optical attenuation had been added to the system. This should not present a practical problem, as long as the "bright" signals are many times the "dark" signals, e.g. 50 mA vs. 1 mA. The actual test current may vary (typically in the range from 0.1 mA to 10 mA), the requirements being that the test current be precisely known, that it be small enough to cause only negligible self-heating of the LED, and that it be large enough so that the current is not dominated by the behavior of surface states in the LED. Whatever test current is used, the waveform of FIG. 4b will work well when "bright" signals are substantially larger than "dark" signals, for example at least 25% larger, and preferably at least a factor of ten larger.

A difficulty could arise, however, in use of this method, when it is necessary to reduce normal LED drive currents substantially in order to perform oximetry on very transparent patients, e.g. those with very small digits. It might be required, for example, to reduce the operating current to something close to the temperature-test current, in which case there would be no significant difference between the drive current and the test current. Difference signals could disappear entirely, or could be reduced so much as to make oximetry measurements very noisy.

An alternative waveform for dealing with this challenge is shown in FIG. 4c. Now there are three periods per half-cycle; a drive period (401c, 403c), a temperature-test period (402c, 404c), and a separate dark-reference period (406c, 408c). Other suitable waveforms will be apparent to those skilled in oximeter circuit design. The key point is that there should be a drive current period during which an oximetry "bright" signal is collected, a period during which a fixed test current is provided, and a period that provides an effective dark reference, at a level significantly different from the drive current. The dark reference period and the test current period may be the same, in the special case that the oximetry drive current is significantly different from the test current (which may even include the unusual case of an oximetry drive current significantly smaller than the temperature test current).

Yet another embodiment for providing temperature calibration, when the desired LED drive levels are low enough to be comparable to the standard test current, is to recognize that when the LED drive is this low it is may not be necessary to monitor temperature. In many oximeters previously manufactured by the assignee of this invention, there is no temperature monitoring, and the maximum current provided to each LED is limited to 50 mA maximum, on a 25% duty cycle. It is known from long experience that drives at this level will not produce high enough skin temperatures to induce a burn, with sensors of the type designed by this manufacturer. Thus, active temperature monitoring may be engaged only when LED drive current exceeds a threshold, such as 50 mA. The fact that this threshold so far exceeds the 1 mA test current means that the waveform of FIG. 4b should always suffice.

Yet another embodiment for providing temperature calibration, when the desired LED drive levels are low enough to be comparable to the standard test current, is to provide temperature calibration curves at multiple small currents, and not just at the commonly used value of 1 mA. As long as a current is small enough to avoid significant self-heating of the LED, and large enough to turn on the LED junction effectively, calibration is possible. Thus when the oximeter is operating at very low LED drive levels, two alternative embodiments become available for obtaining both oximetry and temperature measurement:

The waveform of FIG. 4a may be used, with the drive current being selected to be one of the particular values at which a temperature calibration curve is available. In this case, the drive current itself would be used as the test current for measuring $V_f$ and inferring junction temperature.

The waveform of FIG. 4b may be used, with the test current being always selected, from the available set of test currents at which calibrations exist, to have the largest available difference from the oximetry drive current. For example, if the oximetry drive current were 0.13 mA and the available test currents were 0.1, 0.3, and 1.0 mA, 1.0 mA would be selected.

Figure 5:
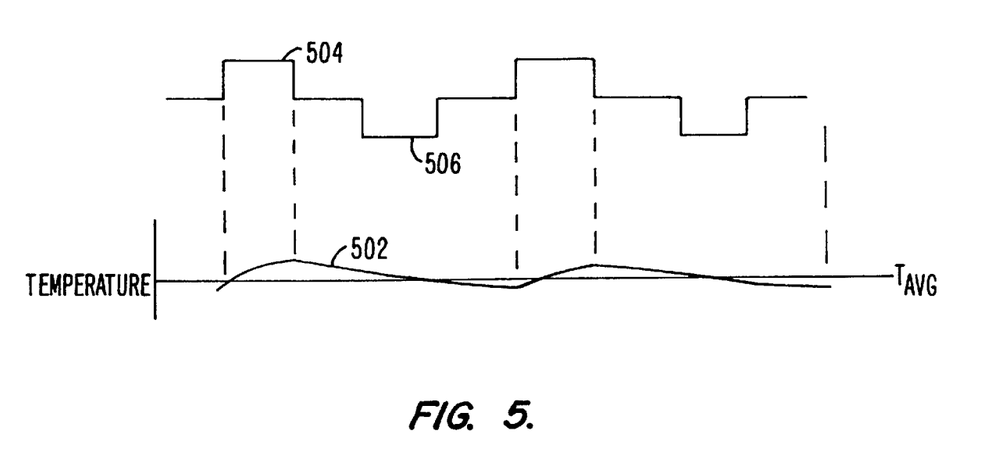
FIG. 5 is a diagram illustrating the fluctuation of LED junction temperature during one drive cycle.

A further refinement comes from recognizing that the temperature of a junction may change noticeably when drive current turns off. FIG. 5 shows one possible response of the junction temperature 502 of a red LED during the oximeter drive cycle. The temperature fluctuates about an average, rising during each drive pulse 504, and decaying during the periods between drive pulses. A temperature-sensing measurement made during the non-drive period will find a temperature that occurred sometime during the drive period, but this temperature may not represent a mathematically convenient value such as the peak temperature reached or the average temperature reached. It may therefore be desirable to sense $V_f$ several times during the non-drive period, and to use the resulting information to estimate what temperature was reached at the beginning or the end of the drive period, or both. For example, a temperature measurement made just before the drive pulse begins will be a good estimate of the temperature at the very start of the drive pulse. To estimate temperature at the very end of the drive pulse, it may be useful to use a method such as that illustrated in FIG. 6. This known method is described in the text accompanying FIG. 12 of National Institute of Standards and Technology Special Publication 400-86, "Thermal Resistance Measurements."

Figure 6:
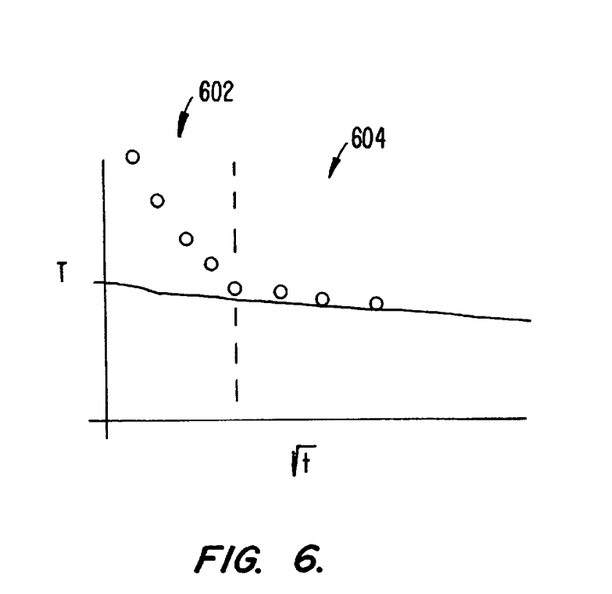
FIG. 6 is a graph illustrating the use of curve fitting to estimate junction temperature at the end of the active portion of an LED drive cycle.

FIG. 6 shows that there is a period 602, after current is switched from drive level to test level, during which electrical transients prevent accurate measurement of temperature. Then there is typically a period 604 during which temperature changes according to a known rule (in many cases being proportional to the square root of time). By fitting a curve to several measurements taken during the latter period 604, it is possible to project back to the ending time of the drive pulse, to estimate the temperature at that time.

Once junction temperature is known, a useful next step in many cases is to use knowledge of the junction temperature to determine the temperature of a patient's skin, immediately beneath the sensor. It is important to ensure by some means that the skin does not get hot enough for a burn to occur, and there may also in some cases be clinical value in knowing the patient's skin temperature. The patient's skin temperature may be determined by independent means, such as by incorporating a thermistor or thermocouple in the oximeter sensor. Alternatively, in some cases skin temperature is estimated with useful accuracy from measurements of the temperature of one or both LED junctions. This embodiment will be explained by referring to FIGS. 2A, 2B, and 2C.

Figure 2A:
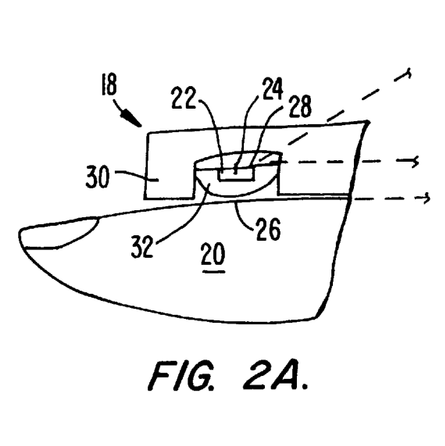
FIG. 2A is a diagram illustrating the heat-sinking path between an LED and a patient.

FIG. 2A is a diagram illustrating a sensor 18 placed upon a patient's finger 20. The junction of the LED 22 is a small region near point 24. The temperature of the junction at point 24 will be different from the temperature at surface 26 of the patient's skin. Most of the heat generated in the LED is produced at or near the P-N junction, and most of this heat will eventually reach the patient's skin, although a portion of the heat enters the air surrounding the sensor. A useful approximation in modeling is to assume that all of the heat is produced exactly at the junction, and that all of it flows to the skin. The temperature difference between the junction and the patient's skin is determined by the values of the series of thermal resistances through which the heat must flow. First the heat spreads from the junction to the entire body of the LED. Then it passes through the die bonding epoxy or solder (not shown) into the supporting leadframe 28. Heat then spreads throughout leadframe 28, and then passes into encapsulation plastic 32. If the encapsulation plastic is in direct contact with the skin, the principal heat flow may then be directly into the skin. If the encapsulant is out of contact with the skin, heat may flow next into sensor body 30, and from there to the skin 26 of the patient's finger. Finally, it should be recognized that because of local tissue heating induced by the sensor, the region of skin immediately under the sensor is likely to be somewhat warmer than the surrounding skin, so that there is another significant thermal resistance associated with the small portion of the patient's skin closest to the emitter (heat flows through this resistance into the cooler surrounding skin). The size of this last thermal resistance will be affected, among other things, by the strength of local blood perfusion, since convective heat transport by flowing blood has an effect similar to that of an increase in thermal conductivity of the nonmoving tissue. In discussing heat transport through tissue, we find it useful to approximate the behavior of the tissue by a simple thermal resistance (which may vary over time), without being concerned about the relative importance of blood convection in determining this effective thermal resistance. We also will not discuss here the further progress of heat into the core of the patient's body, and from the patient's skin into the surrounding air, but rather will simply treat the skin as a heat sink.

Since we are concerned with estimating the patient's skin temperature from measurements of junction temperature, we need to determine the difference between junction temperature and skin temperature. We use the known method of describing heat flow by analogy to Ohm's law, in which temperature difference $\Delta T$ across a body is analogous to voltage in Ohm's law, thermal power flow P through the body is analogous to current, and thermal resistance $R_\theta$ is analogous to electrical resistance. Thus, for any particular body through which heat flows in one dimension;

$$\Delta T = P^* R_\theta \quad (1)$$

The difference between junction temperature and skin temperature may be calculated as the sum of temperature drops $\Delta T_i$, across the series of segments of materials of different kinds through which heat flows enroute from the junction to the patient's skin. When time-dependent heat flows are to be modeled dynamically, it is common to use capacitive circuit elements in parallel with the thermal resistances, these capacitors representing the heat capacity of the bodies which they simulate. The capacitive values are not needed in modeling of steady-state heat flows, because in such heat flows, there is no change with time in the amount of locally-stored thermal energy.

One particularly simple way to employ an Ohm's-law thermal model is to compute the quasi-steady-state junction-to-skin temperature difference by using a single assumed value of total thermal resistance, characteristic of a particular model of sensor. The oximeter is provided (for example by encoding means in the sensor connector) with information as to which model of sensor is in use (so that the oximeter may look up thermal resistance in a table), or the oximeter is provided directly with an appropriate thermal resistance value (for example by a ROM chip incorporated in the sensor connector). Knowing the current which it is putting through the LED junction, and the voltage $V_f$ across that junction, the oximeter computes power dissipation P, permitting it then to derive $\Delta T$ from Equation (1) above. In order to avoid risk of burning the patient, the assumed value of thermal resistance must be the lowest that could practically occur, so that the resulting estimate of skin temperature will always err on the high side.

Skin temperature can be estimated more accurately if it is possible for the oximeter to determine from time to time what is the actual effective thermal resistance between the junction and the skin surrounding (but not immediately under) the emitter. This directly-determined thermal resistance value may account for differences in thermal resistance among different sensors of a particular model, and (more importantly) for the large differences that can occur in effective thermal resistance of the portion of the patient's skin which underlies the emitter. Patients will differ from one another in this regard, and any single patient will exhibit differences over time, at least because of normal fluctuations in local blood perfusion.

Figure 2B:
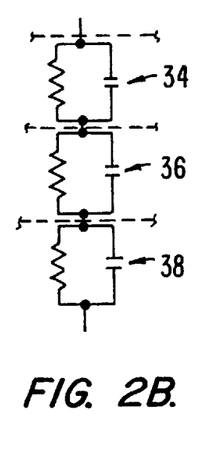
FIG. 2B is an electrical diagram illustrating a modeling of the thermal resistance of the paths of FIG. 2A.

FIG. 2B illustrates one way of modeling the thermal impedance between the junction of the LED and the patient. Circuit 34, shown as a resistor and capacitor in parallel, represents the thermal resistance and heat capacity of the lead frame. Circuit 36 represents the thermal resistance and heat capacity of the encapsulating plastic and sensor body, while circuit 38 represents the thermal resistance and heat capacity of the portion of the patient's skin, close to the emitter, which is elevated in temperature above the surrounding skin because of heat input from the emitter. Not shown are faster-responding portions of the thermal "circuit", such as the thermal impedances of the body of the LED chip and the die bonding material. If data are collected during very short time intervals after switching off the LED operating current, it may prove desirable to provide additional RC elements to represent these impedances.

Figure 2C:
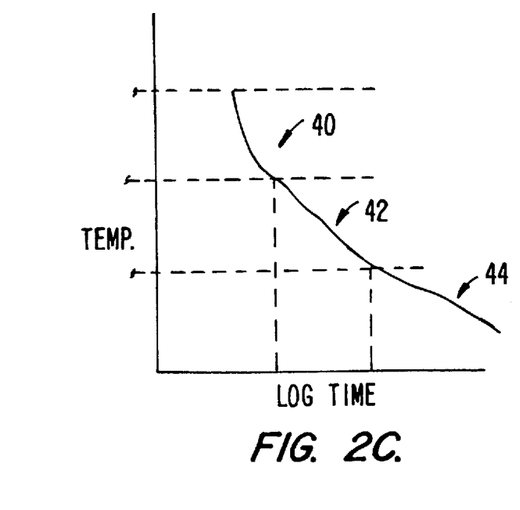
FIG. 2C is a graph of the temperature versus time characteristics of the different thermal impedance regions of FIG. 2B.

FIG. 2C is a graph of the sort of temperature versus time behavior which may be exhibited by the circuit of FIG. 2B, if oximetry is temporarily suspended for a period of several seconds, so that the thermal response of the junction can be observed over this long a period. During time period 40, circuit 34 is most important in determining the decay. Then, during time period 42, circuit 36 is most important, and finally, during period 44, circuit 38 is most important. The order in which these circuits achieve their greatest importance is set by their relative speed of thermal decay. The lead frame tends to respond fastest, because its metal material is of relatively high thermal conductivity and because its mass is small. The plastic encapsulant has relatively low thermal conductivity, but is of small mass, so its response tends to come next, and finally the human tissue, which is of low effective thermal conductivity and has a relatively large mass, is slowest. In fact, for particular conditions, the relative speeds of different decay components may change and the shapes of the resulting curves may change accordingly. In particular, the effective thermal conductivity, and hence the thermal response time of skin, varies dramatically as the extent of local perfusion changes. In any event, one process for determining the effective thermal conductivities and heat capacities of the different components of the thermal "circuit" is to measure junction temperature at a series of discrete times and then fit to the observed data a theoretical curve derived from an appropriate model. For the circuit model of FIG. 2B, an appropriate mathematical model is a sum of exponential decays. Having fitted such a model, by known methods, the effective thermal impedances are determined. The impedances so determined are then used to estimate skin temperature on a continuing basis, from a knowledge of junction temperature and junction heat generation, as noted above.

The method just described requires suspension of normal pulse oximetry operation from time to time, in order to determine the appropriate values of thermal resistance, especially the effective thermal resistance of the patient's skin. To ensure that clinically important desaturations are not missed, there is a limit on the length of time for which oximetry may safely be suspended. An alternative embodiment introduces a known change in power dissipation without suspending oximetry. For example, the drive current to LEDs may be temporarily halved and the detector-channel gain temporarily doubled, so as to maintain approximately the same oximetry signal levels and continue oximetry operation, while the effect of the power-input step on junction temperature is tracked over time. This embodiment produces essentially the same information as does suspending oximetry, at the expense of increased complexity of product design and manufacture.

Figure 3:
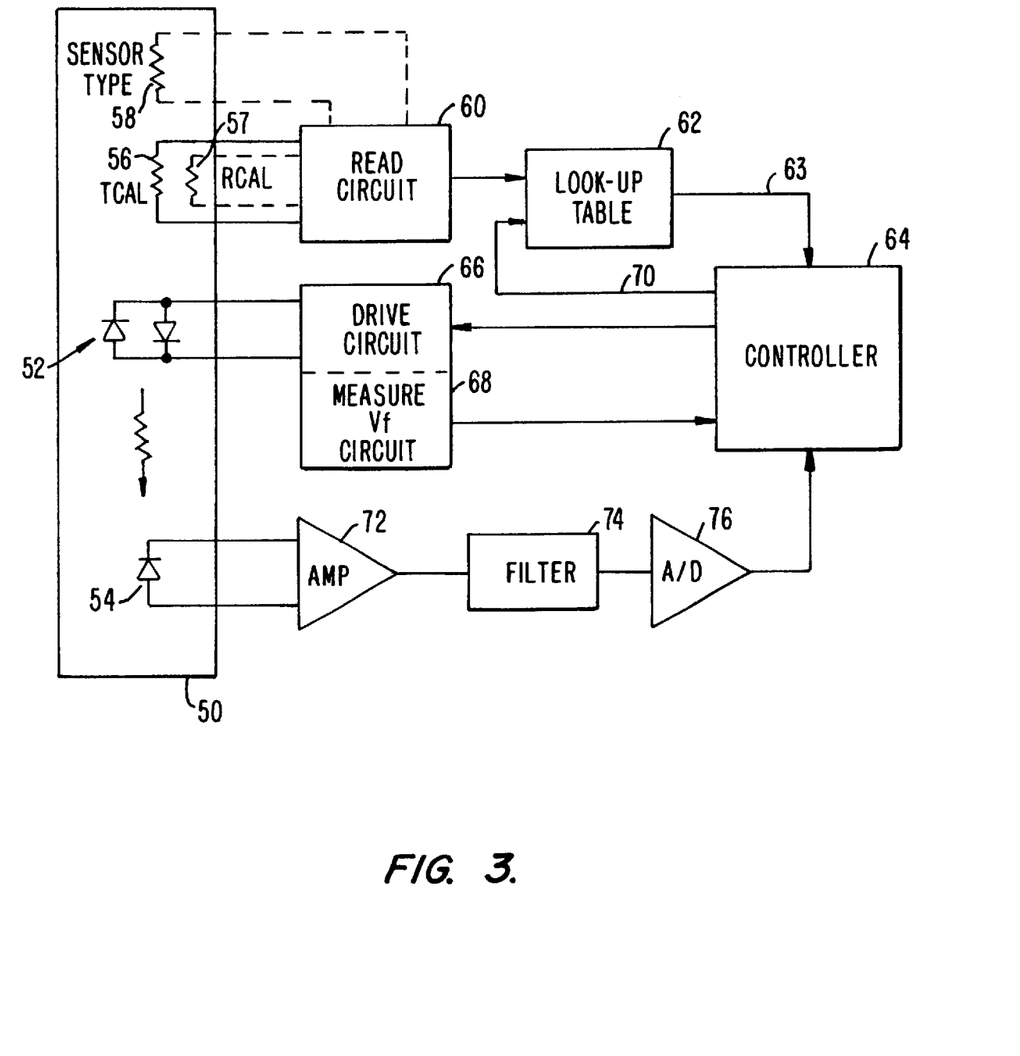
FIG. 3 is a block diagram of an oximeter system according to the invention incorporating a temperature calibration resistor in the sensor.

FIG. 3 is a block diagram of a system according to the invention. A sensor 50 includes red and infrared LEDs 52 as in the prior art, along with a detector 54 and a wavelength calibration resistor (RCal) 57. In addition, a temperature calibration resistor 56 is added according to the present invention, along with an optional resistor 58 for identifying the sensor type.

A read circuit 60 is provided for reading temperature calibration resistor 56, and optionally sensor type resistor 58. The value is provided to a look-up table 62 to determining the appropriate curve as illustrated in FIG. 1. This is then provided to a controller 64.

Controller 64 provides signals to a drive circuit 66, to control the amount drive current provided to LEDs 52. The invention adds a measuring circuit 68 for measuring the forward voltage $V_f$ of at least one of the LEDs, providing that value to controller 64. This allows the controller to adjust the drive current in accordance with the actual estimated junction temperature. The actual temperature can be estimated by using a calibration curve derived from look-up table 62 to convert the measured value(s) of $V_f$ from measurement circuit 68 to a temperature. Coefficients required to compute the calibration curve, or points of the calibration curve itself, are accessed by the controller from look-up table 62 through line 63.

Alternately, or in addition, the estimated skin temperature is derived from junction temperature measurements, as noted above, and the skin temperature is provided to the algorithms controlling LED currents.

Detector 54 is connected through an amplifier 72 and a filter 74 to an A/D converter 76. As in the prior art, this can form a feedback path, in which controller 64 uses computations based on the output of A/D converter 76 to adjust the LED drive current to optimize the intensity range of the signal received. Ideally, the signal should be well within the range of A/D converter 76 for both the red and infrared LEDs (e.g. one rule which may be applied is to adjust LED drives and amplifier gains so that both signals fall between 20% and 80% of full scale reading of converter 76.) The present invention adds a feedback control to permit the LED drive current to be increased to a value which optimizes the signal to noise ratio, without exceeding a maximum allowable temperature for the patient.

More particularly, in one embodiment the normal operating mode of the LED drive level control implemented by controller 64 implements the following simultaneously-active rules. In applying rules 2, 3, and 4, the one requiring the lowest limit on drive current is the rule which dominates.

1) Adjust the balance of the two LED drives so as to produce detected red and IR signals that are of similar size (e.g., so that their ratio falls within the range of 0.8 to 1.2).
2) While maintaining the indicated balance, increase the level of both LED drives until an adequate signal to noise ratio (S/N) is achieved (or, alternatively, until further increase in LED drive levels would not significantly increase S/N). In the interest of conserving battery life in battery-powered instruments, this drive adjustment is likely to be made in concert with adjustments of the gain of detector amplifier 72, so as to achieve the desired S/N with the lowest practical LED drive.
3) Do not permit LED drive levels to exceed values that would unacceptably shorten the lives of LEDs. The acceptable level may be different for reusable sensors than for disposable sensors, since reusable sensors are required to last longer. A suitable maximum current for each type of sensor may be provided as a digitally encoded value from a digital storage chip incorporated in the sensor assembly, or the current may be taken from a look-up table incorporated in the oximeter, where the appropriate entry in the table is selected based on a sensor type code provided by an element of the sensor assembly.
4) Apply one of the following temperature-control rules:
   a) Do not cause the patient's skin temperature to exceed a predetermined safety threshold, or
   b) Do not permit the integrated time-temperature exposure of the patient's skin to exceed a predetermined safety threshold (since it is known that higher temperatures can be tolerated safely if the exposure is short), or
   c) Do not permit the LED junction temperature to exceed a predetermined safety threshold (e.g., since the junction always runs warmer than the skin, limiting the junction to 41° C. will certainly avoid driving the skin above this level).

When a sensor according to the present invention is applied to a patient having poor peripheral perfusion, so that it is difficult for a pulse oximeter sensor to achieve a high signal to noise ratio, the effect of operating the feedback control system embodied in the above rules will typically be for the oximeter to drive the patient's skin temperature to a value just below the predetermined safety threshold, and to hold it near that point. Thus the measurement will benefit from the increase in light output of the LEDs to the largest value that is consistent with avoidance of skin burns, and may also benefit from a local perfusion increase (which tends to increase percentage modulation in the detected oximetry signal), as a result of local heating of the skin.

As can be seen, the present invention thus allows the intensity of the LEDs to be optimized, without risking burning the patient, and without being constrained to an arbitrary maximum limit for the most conservative range of LED values.

A sensor according to the present invention can be used in a number of ways. In a first embodiment, a temperature calibration (T-cal) resistor such as 56 in FIG. 3 is read, and the drive circuit is controlled solely in accordance with this to provide the outcome intensity. This is to say that T-cal resistor 56 communicates to the controller that a particular calibration curve is to be applied for the relationship between junction temperature and $V_f$, and no further information is provided to the oximeter regarding proper current-control strategies for this particular sensor.

In a second embodiment, the drive current value is optimized further by encoding a sensor type with a resistor 58. Knowing the sensor type, the oximeter has better knowledge of the maximum allowable current for the particular sensor, or has better knowledge as to the appropriate thermal impedance values to use in making calculations. Please note that the calibration resistors 56 and 58 are but one example of encoding, which could be done by active circuits, digital codes, a single resistance, an A/C impedance, or any number of other encoding techniques.

The present invention allows determination of the estimated temperature at the patient's skin. This is done as described above, including using an estimated thermal resistance between the junction of the LED and the patient's skin.

Other benefits arise from being able to determine the junction temperature. For example, the junction temperature of the LED may be high if there is poor contact with the patient or if the detector is off the patient, since the patient's skin will not be available for heat sinking purposes. This may be especially relevant in reflectance-type sensors, in which improper application of the sensor may lead to measurement error caused by optical shunt (passage of light from the emitter to the detector without passing through the patient's tissue). In one embodiment, the oximeter is programmed so that if it observes an unexpectedly high junction temperature, or an unexpectedly high thermal resistance between the junction and its ultimate heat sink, it will automatically generate a "sensor off" signal or other warning signal to the clinician.

In one embodiment, a further benefit of measuring the junction temperature of an LED, especially the red LED in an oximeter, is that knowledge of the junction temperature is used to correct the oximetry calibration of the oximeter, or to select a more accurate calibration curve from among several available predetermined curves. It is known that the wavelength emitted by LEDs shifts with temperature, and that the oximetry calibration shifts when wavelength shifts. While this shift is generally small, it is beneficial in some circumstances to take it into account. U.S. Pat. No. 4,913,150 disclosed the general principle of setting oximeter calibration in accordance with an observed sensor temperature. That patent, however, discloses the monitoring of temperature by means of a separate temperature sensing element. The new method of temperature monitoring disclosed herein is inherently more accurate, because it determines the temperature of the semiconductor junction, which is the region that determines the wavelength of emission.

Figure 7A:
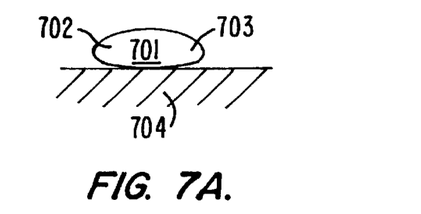
FIGS. 7A and 7B are a schematic drawing of an emitter in contact with a patient's skin, and a graph of the resulting temperature distribution.
Figure 7B:
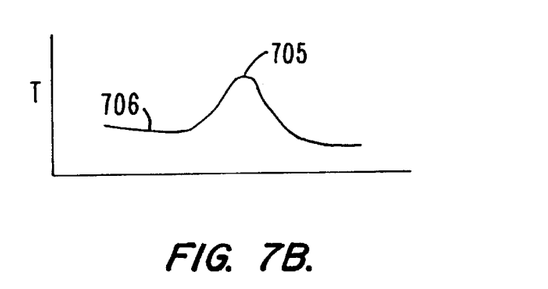
Figure 7C:
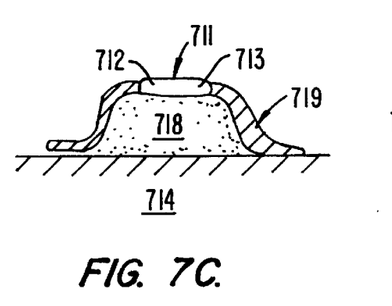
FIGS. 7C and 7D are a schematic drawing of an emitter connected to the patient's skin by a structure comprising two materials, one of which has higher thermal conductivity than the other, and a graph of the resulting temperature distribution.
Figure 7D:
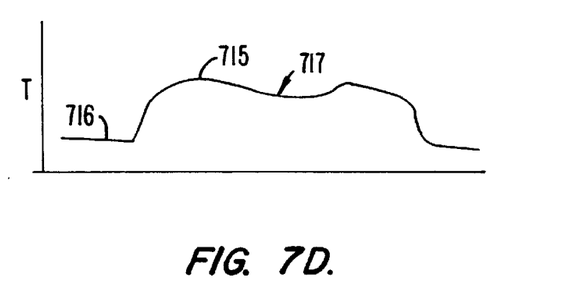

This new method of selecting or adjusting oximeter calibration in response to observed junction temperature is of particular value when used with heat-spreading oximetry emitters configured as in FIGS. 7B, 7C, and 7D. The construction of the emitters shown in these figures may be understood by comparison with FIG. 7A, which illustrates a conventional emitter structure.

In FIG. 7A, emitter capsule 701, which may be of epoxy resin, contains the one or more LEDs (not shown) which emit the light required for a medical sensing application, these LEDs typically being located close to the center of the capsule. Electrodes, typified by 702 and 703, bring current to these LEDs, causing light emission and concomitant heat production. As the heat flows to the patient's tissue 704, it will typically concentrate in a region of tissue close to the LEDs, producing a distribution of tissue temperature like that shown in FIG. 7B. There will be a peak temperature 705, exceeding the typical temperature 706 of surrounding tissue. Because of the relatively high concentration of heat delivery in the peak region near the center of the emitter, this configuration requires rather stringent limits on the power that can be delivered to the emitter capsule, lest peak temperature 705 get high enough to cause a burn (which is thought to be possible, in some patients, when peak temperature 705 reaches 43° C.). An advantage of the configurations shown in FIGS. 7C, 7E, and 7F is that they reduce the concentration of heat delivery, thus permitting more power to be delivered to the emitter without risking a burn, and thus permitting a higher light level to be created (which typically enhances the signal to noise ratio of the medical instrument).

In the device of FIG. 7C, emitter capsule 711 contains one or more LEDs (not shown), and has electrodes typified by 712 and 713. A low-thermal conductivity material 718 spaces the emitter capsule from tissue 714. Surrounding structure 719, made of a material having higher thermal conductivity than the material of capsule 711, provides the primary thermal conduit from capsule 711 to tissue 714. Examples of suitable material for spacer 718 are silicone rubber and air. Examples of suitable material for surrounding structure 719 are copper and molded alumina. As shown in FIG. 7D, the effect of this configuration is that peak tissue temperature 715 will tend to develop in an annulus, because heat delivery to the tissue is greatest here. Because heat delivery is less concentrated than in FIG. 7A, it will be possible to deliver more power to the LEDs in emitter capsule 711 before peak temperature 715 exceeds typical surrounding-tissue temperature 716. Tissue temperature 717, in the center of the structure, may be comparable to temperature 715 or may be somewhat depressed by comparison.

Figure 7E:
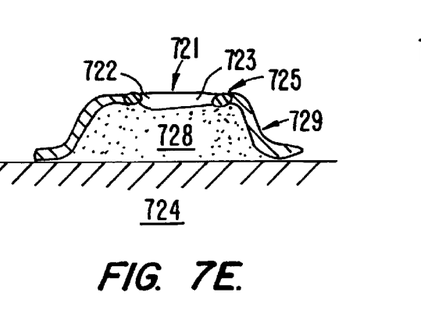
FIG. 7E is a schematic drawing of an emitter connected to the patient's skin by a structure comprising a central region of low thermal conductivity and a surrounding multi-material structure of higher thermal conductivity.

FIG. 7E is a diagram of one embodiment showing the high-thermal-conductivity surrounding structure made of several components, which is effective so long as there is a good thermally-conductive path from capsule 721 to tissue 724. In this particular case, low-conductivity material 728 is surrounded by high-conductivity material 729, which is joined by a bead 725 of thermally-conductive epoxy to capsule 721. Power is delivered to the LEDs in capsule 721 by electrodes, typified by 722 and 723.

Figure 7F:
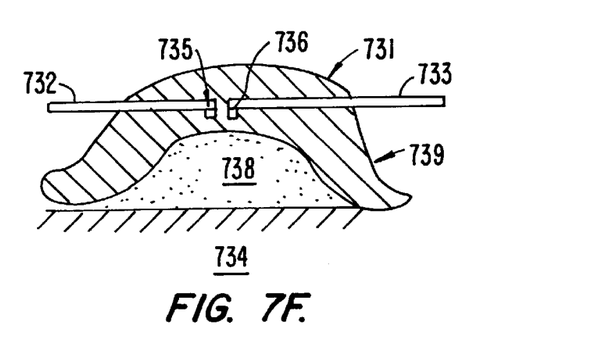
FIG. 7F is a schematic drawing of an emitter connected to the patient's skin by a generally annular integral extension of the emitter capsule, the space in the annulus being filled with a material of lower thermal conductivity than that of the capsule.

FIG. 7F is a diagram of an embodiment where the thermally conductive path from the LEDs to the tissue is through an structure integrally molded with the emitter capsule. In this case, we show LEDs 735 and 736, mounted on leadframe elements 732 and 733. Emitter capsule 731 is molded of epoxy resin. An integral portion of capsule 731 is standoff ring 739, which rests on tissue 734 in an annular contact region. The open central portion of standoff ring 739 is filled with a material 738 of lower thermal conductivity. Material 738 may be air or may be a plastic material of lower thermal conductivity than the epoxy of capsule 731. One noteworthy point about this embodiment is that while epoxy resin is not usually considered a material of high thermal conductivity, the fact that it has higher conductivity than does material 738 will tend to direct heat flow into an annular region rather than into a central region, and this will tend to reduce the peak tissue temperature produced at any given level of power delivery.

Part of the benefit of the structures exemplified by FIGS. 7C, 7E and 7F may be obtained in the absence of a surrounding structure of high-thermal-conductivity material. Thus, for example, if the structure of FIG. 7C were built without surrounding part 719, there would still be some heat-spreading benefit provided by the presence of the spacing low-conductivity material 718. Because the LEDs within capsule 711 are held further away from tissue 714 because of the presence of material 718, there will be more opportunity for heat to spread out enroute to the tissue than there is in the structure of FIG. 7A, so that temperature peak 705 will tend to be broader and lower. Still, it will generally be preferable to provide a surrounding structure of higher thermal conductivity than the core structure, so as to divert as much heat as possible away from the "hot spot" which typically occurs close to the location of the LEDs in an emitter assembly.

As noted above, the use of junction temperature data to influence the selection or computation of calibration curves for an LED-based sensor will be of particular value when structures such as those of 7C, 7E, and 7F are used. This is true because the additional spacing components, such as 718 and 719, which separate emitter capsule 711 from the tissue, will reduce the tendency of the tissue to act as a temperature stabilizer for the LEDs. Tissue temperature in many cases is fairly stable, in a range such as 25° C. to 35° C., and in the structure of FIG. 7A, which brings the LEDs close to tissue 704, the relatively low thermal resistance between LEDs and tissue will tend to pull LED temperature toward tissue temperature. The structures of FIGS. 7C, 7E, and 7F increase the thermal resistance between the LEDs and the tissue, so that LED temperature will swing more widely. At very low LED drive currents, the LED junctions will run closer to the temperature of the surrounding air, and at high LED drive currents, the LEDs junctions will run further above the temperature of the tissue, than would be the case in the structure of FIG. 7A. This increased swing in junction temperature will increase the tendency of LED wavelength to vary, and will increase the value of a means of taking wavelength variation into account in establishing instrument calibration.

Throughout this patent application, in the interest of clear communication of the essential features of our invention, we have omitted from figures and from the corresponding discussions many of the known details of practical sensor design. This is particularly evident in FIGS. 7A through 7F, in which, for example, no details of such components as bandages, adhesive layers, connecting cables, or detectors have been shown. The appearance of the sensor in the immediate vicinity of emitter assemblies such as those illustrated might especially be altered by the incorporation of thin layers of adhesive material, or of adhesive-coated plastic film, between the emitter assembly and the patient's tissue. The presence of such additional materials would not compromise the essential aspects of this embodiment of our invention.

It is necessary, in the design of a system for monitoring temperature by measuring junction voltage, to avoid excessive increases in the electrical resistance of leads and connections, which could lead to inaccurate temperature measurement. For example, if 1 mA test current is used to monitor temperature, and if a bad crimp connection induces a 1 ohm excess resistance, this will cause the measured value of $V_f$ to be high by 1 mV. If the temperature calibration of the junction is about –2 mV/° C., the resulting temperature measurement will be low by 0.5° C. Since false low temperature readings increase the risk of burning a patient, it is important to minimize such errors. One way to avoid any ill effect of excessive lead resistance is to provide a four-wire measuring configuration, as shown schematically in FIG. 8.

Figure 8:
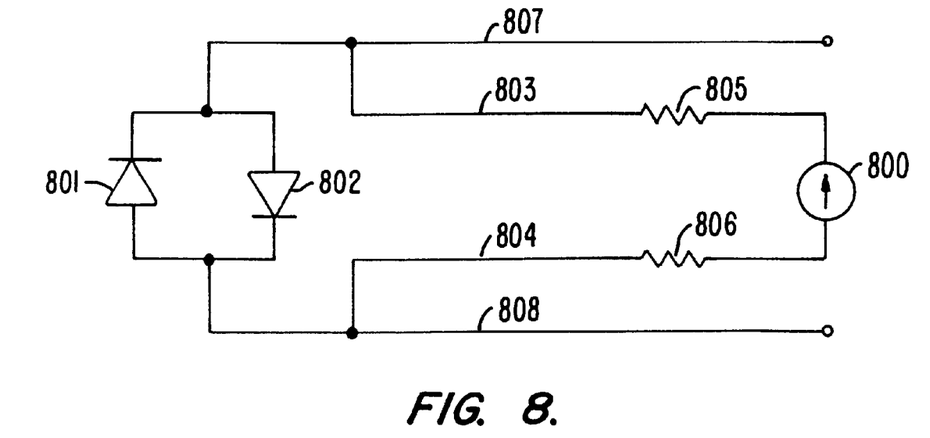
FIG. 8 is a schematic diagram illustrating the use of four-wire voltage measurement to enhance accuracy in determining LED junction temperature.

In FIG. 8, current source 800 provides drive current to LEDs 801 and 802, through leads 803 and 804, having in-line resistances 805 and 806 (attributable to connections and wire resistance). Leads 807 and 808, which carry very little or no current are used to measure $V_f$ at a point close to the LEDs, so that the effect of resistances 805 and 806 on voltage measurement is negligible, and any resistances in series with leads 807 and 808 are also unimportant because they carry so little current. It may not always be economical to carry extra wires such as 807 and 808 all the way to the emitter capsule of a pulse oximeter sensor, but it will often be advantageous to carry such auxiliary leads to a point closer to the emitter than the terminals of the LED drive transistor. For example, in an oximeter which connects to sensors through a long extension cable, the extra voltage-sensing wires may beneficially be extended through the extension cable to the point where the sensor's own cable attaches.

Other safety precautions may be applied in the design of the oximeter. For example, to avoid burning the patient, a maximum current limit can be imposed to avoid generation of excessive current. To protect against short circuits in the system, which might be caused (for example) by fluids spilled on the sensor, the oximeter might be programmed to stop LED drives and present an error warning if an unexpectedly low resistance is observed.

Figure 10:
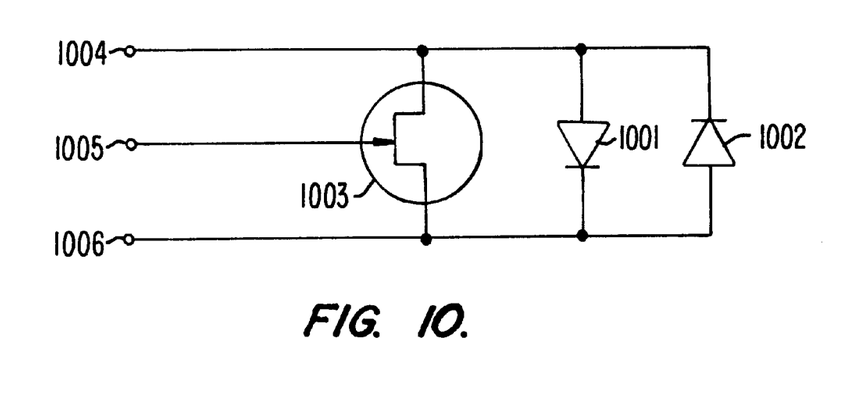
FIG. 10 is a schematic diagram illustrating the use of a MOSFET switch to permit independent measurement of emitter lead resistance.

A circuit configuration which permits separate monitoring of lead resistance is shown schematically in FIG. 10. Connected in parallel across red LED 1001 and infrared LED 1002 is MOSFET switch 1003. Connections 1004 and 1006 permit the application of LED drive currents and LED temperature sensing currents, and may additionally be used for lead resistance measurement as will be explained below. Connection 1005 permits application of a control voltage to switch MOSFET 1003 into either its high-resistance or low-resistance state.

During normal operation of the LEDs, for oximetry or temperature measurement, MOSFET 1003 would be in its high impedance state, and would have negligible effect on system performance. To sense lead resistance, from time to time oximetry and temperature sensing would be suspended, and MOSFET 1003 would be switched into its low resistance state. A current, possibly the same as the $V_f$ measurement current near 1 mA, would be sent through leads 1004 and 1006. Because the resistance of a properly selected MOSFET is in the milliohm range, almost all the current would pass through MOSFET 1003 rather than through either LED, and the circuitry normally used to measure $V_f$ could instead be employed to measure the voltage drop across the leads, permitting a computation of lead resistance. This measurement could be used to determine whether an unacceptably high or low lead resistance existed (with the oximeter producing an error indication in this case), or could simply be used to correct measurements of $V_f$ to more accurately determine actual LED voltage, by computationally removing the effect of lead resistance.

MOSFET 1003 could be located in the sensor head, close to the LEDs, in which case it would be positioned to sense the combined resistance of wires and of the crimped or soldered terminating connections of these wires in the connector joining the sensor assembly to the oximeter. Alternatively, MOSFET 1003 could be located in the connector of the sensor assembly. This would position it to monitor the resistance of connections, and would have the advantage of not requiring the cost of an added wire in the sensor cable.

Figure 11A:
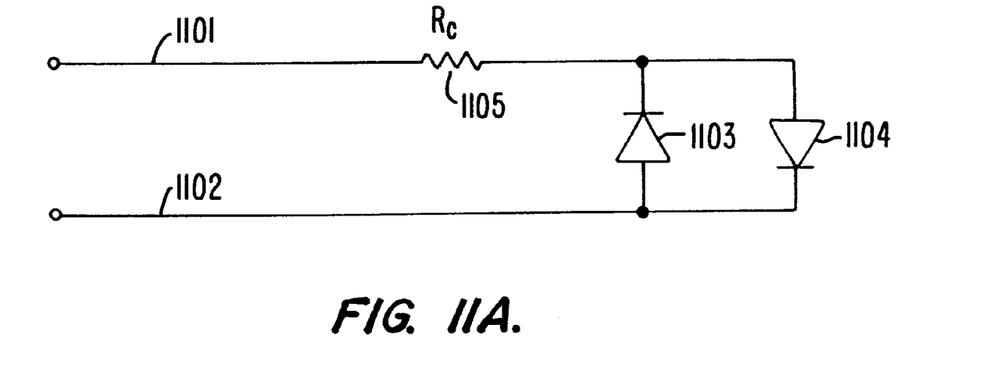
FIG. 11A is a schematic diagram of a two-LED sensor connected to an instrument by leads having serial connection resistance.
Figure 11B:
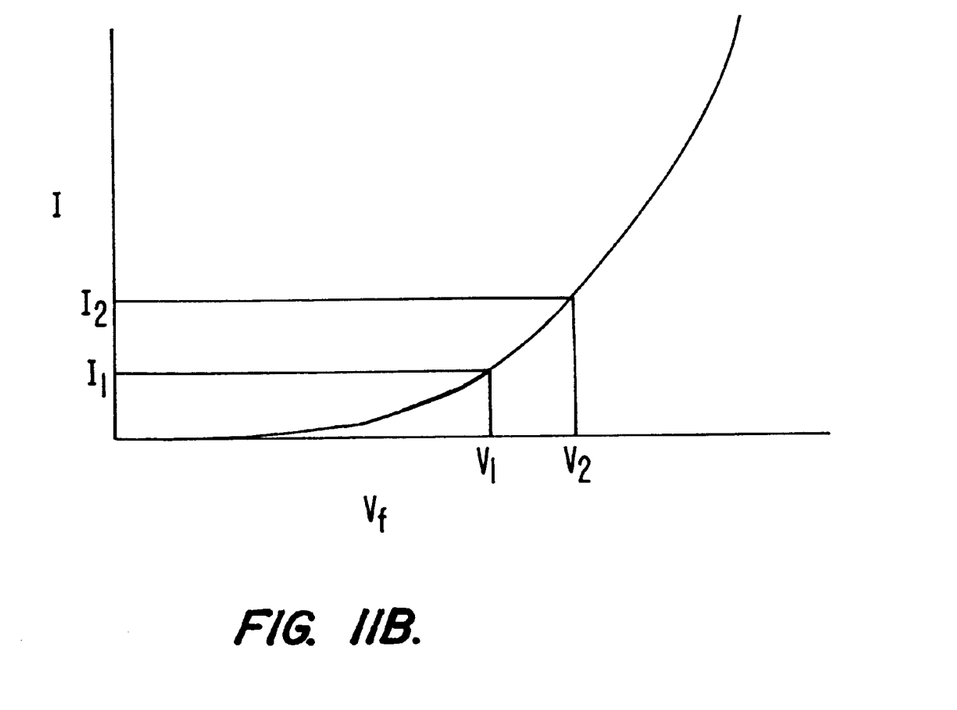
FIG. 11B is an I–V characteristic of one of the LEDs of FIG. 11A.

FIGS. 11A and 11B illustrate a method of measuring in-line resistance which does not require the use of an auxiliary element such as MOSFET 1003. This method is based on measuring $V_f$ at two different currents. In FIG. 11A, current is provided through leads 1101 and 1102 to back-to-back LEDs 1103 and 1104. An unknown connection resistance 1105 is contributed to the circuit by wiring and (possibly imperfect) connections. Resistance 1105, whose value is $R_c$, is to be determined. Also shown in FIG. 11B is the characteristic curve of one of the LEDs, e.g. 1104. That LED is probed successively by two different test currents, $I_1$ (e.g. 0.5 mA) and $I_2$ (e.g. 1.0 mA), so that the corresponding voltages developed across the LED itself are $V_1$ and $V_2$. At the instrument end of leads 1101 and 1102, the two observed voltages are:

$$V_{i1}=I_1R_c+V_1$$

$$V_{i2}=I_2R_c+V_2$$

If the dynamic resistance $R_d$ of LED 1104 is known, in the vicinity of the chosen test currents, then we can compute $$V_2=V_1+R_d*(I_2-I_1)$$

We now have a system of three equations in which we can solve explicitly for $R_c$.

The value of $R_d$ may be determined once for all LEDs of a particular model, so that appropriate values of $R_d$ may be stored in an oximeter instrument for each sensor model which the instrument is programmed to recognize. Alternatively, the value of $R_d$ may be carried explicitly in a memory means such as a digital chip which is incorporated in the sensor. Yet another possibility is to incorporate in the sensor a coding means, such a resistor selected from a list of values, each value representing a possible range of dynamic resistances of the LED incorporated in that sensor. Table 3 is an example of such a list of values.

TABLE 3

| Coding resistor, ohms | LED dynamic resistance, ohms |
| --- | --- |
| 100 | <1.00 |
| 200 | 1.00 to 1.99 |
| 300 | 2.00 to 2.99 |
| 400 | 3.00 to 3.99 |
| 500 | 4.00 to 4.99 |
| 600 | 5.00 to 5.99 |
| 700 | 6.00 to 6.99 |

In several of the embodiments of our invention described above, an encoding device has been incorporated in the sensor assembly, to communicate to the oximeter instrument the temperature calibration of an emitter or other temperature-sensitive element of the sensor assembly. In an alternative embodiment of the invention, the individual differences in temperature calibration are compensated by incorporating a selectable or adjustable element, such as a trimmable resistor, in series with the temperature sensitive element.

Figure 9:
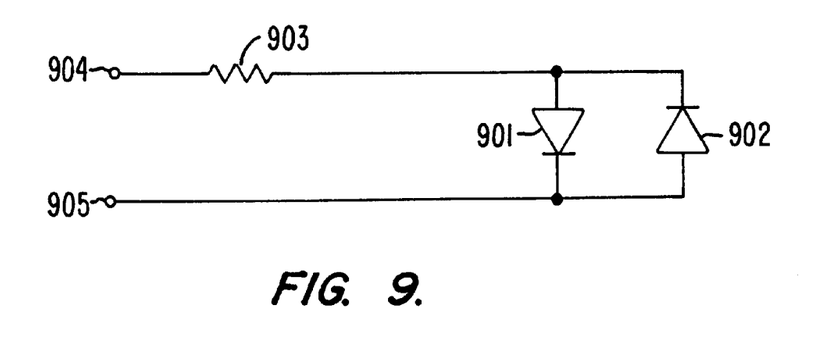
FIG. 9 is a schematic diagram illustrating the use of an adjustable circuit component to allow different LEDs to be used with a common temperature calibration curve.

In FIG. 9, for example, are an emitter comprising red LED 901 and an infrared LED 902, connected back-to-back, both in series with trimmable resistor 903. Connection is made to the emitter through terminals 904 and 905. During manufacture, the voltage between terminals 904 and 905 is measured, with LED 901 forward-biased by a predetermined test current, while this LED is in an environment controlled at a particular temperature such as 40° C., and the value of resistor 903 is adjusted to bring the measured voltage to a predetermined value. Thus, when this emitter is used as part of an oximetry sensor connected to an oximeter, the oximeter will be able to interpret a particular observed forward voltage as representing exactly 40° C., and will be able to estimate other temperatures from observed values of forward voltage by using an estimated sensitivity factor, such as −2 mV/° C. The sensitivity factor used may be an approximation applied to all LEDs, or may be particular to a certain class of LED if the sensor is provided with means to communicate to the oximeter which class of LED is in use.

Our invention has been described above in a particularly efficient form which takes advantage of the ability of a semiconductor junction to sense temperature. Many of the benefits of the invention can be realized by an embodiment in which temperature is measured by a separate device, such as a thermocouple or thermistor, located so as to sense the peak temperature of the patient's skin under the emitter, or to sense the temperature of another point, from which the peak skin temperature can be deduced. For such an embodiment to be practical in high-volume manufacturing, it will usually be necessary to incorporate in the construction of an oximetry sensor an encoding means to inform the oximeter of the correct calibration to use in reading the separate temperature sensor. Such embodiments, which trade an increased cost of material for more straightforward engineering and manufacturing, are contemplated within the scope of the invention.

Figure 12A:
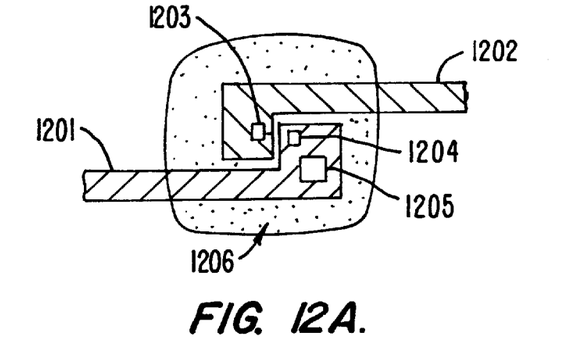
FIG. 12A is a plan cross sectional view of an emitter capsule containing two LEDs and a thermistor.
Figure 12B:
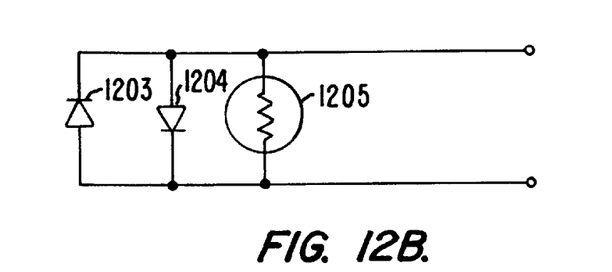
FIG. 12B is a schematic diagram of a thermistor wired in parallel with a pair of back-to-back LEDs.

One example of an embodiment with an independent temperature sensor appears in plan cross-section in FIG. 12A. In this device, leadframe elements 1201 and 1202 support LEDs 1203 and 1204. Thermistor element 1205, which may have a nominal resistance of 2.5 kilohms at 37° C., is mounted together with LED 1204 on leadframe element 1201. Encapsulant 1206 surrounds and protects active elements 1203, 1204, and 1205. FIG. 12B shows that, with this sort of mounting, it would be straightforward to wire thermistor 1205 in parallel with the LEDs. By measuring the resistance of the thermistor with a very small probing current, it is possible to measure its resistance, and hence the temperature of the leadframe, without undue distortion of the measurement by the presence of the LEDs. In order to achieve acceptable manufacturing cost, the nominal resistance of thermistor 1205 might vary as much as +/−10% from its nominal value. Its precise measured resistance, including any effect of the LEDs in parallel with it, could be measured in the factory at a reference temperature such as 37° C., and that resistance could be incorporated in an encoding means as noted above.

Figure 12C:
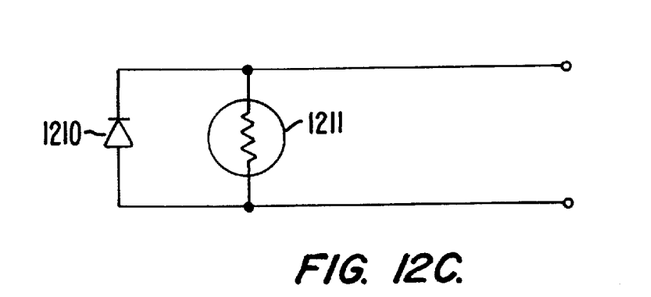
FIG. 12C is a schematic diagram of a thermistor wired in parallel with a detector photodiode.

FIG. 12C shows that a thermistor 1211 could also be wired in parallel with the detector photodiode 1210 of a typical oximeter sensor. By probing thermistor resistance with a current whose polarity is such as to back-bias the detector, the influence of the diode on resistance measurement could be reduced. A detector wired in this way need not be physically mounted together with the detector chip. It might instead, for example, be mounted so as to be in close proximity to the "hot spot" under the emitter.

Figure 13:
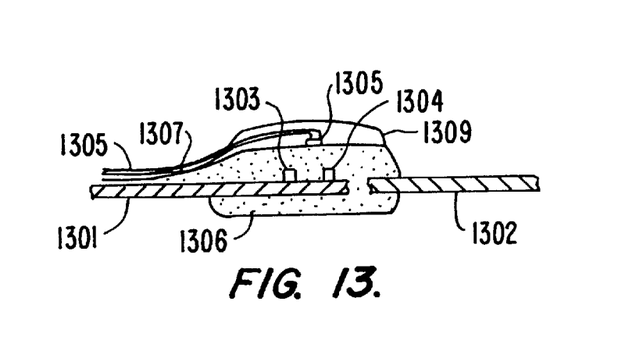
FIG. 13 is a vertical cross sectional view of an emitter capsule containing two LEDs, with a separately wired temperature sensor attached to the capsule on the side toward the patient's skin.

FIG. 13 shows, in vertical cross-section, an emitter assembly with a separately-wired temperature sensing element which is positioned so as to be very close to the patient's skin. This assembly is similar to that of FIG. 12A, except that the temperature sensing element is positioned and wired differently. Lead frame elements 1301 and 1302 support LEDs 1303 and 1304, which are protected by transparent encapsulant 1306. Temperature sensing element 1305, which may for example be a thermistor or a thermocouple junction, is mounted on the surface of encapsulant 1306, and is protected by additional very thin transparent encapsulant layer 1309. Alternatively, transparent layer 1309 may be a thin adhesive-coated plastic film. A suitable thickness for layer 1309, above element 1305, is less than 0.020", preferably less than 0.010", and most preferably less than 0.005". Wires 1307 and 1308 connect to the two electrical terminals of sensing element 1305. While it may appear that element 1305 and its attached wires will substantially limit the light from LEDs 1303 and 1304 which can reach the patient's tissue, in fact enough light will bypass the sensing element so that this will not significantly impede proper oximetry operation.

In another group of embodiments of the present invention, the detector diode of the oximeter sensor is calibrated as a temperature sensor, and its calibration is communicated to the oximeter by encoding means incorporated in the sensor assembly. While the detector diode does not itself deliver a significant amount of heat to the patient, temperature sensing by the detector will be useful under some circumstances. Because of the lack of significant heat flow between the detector and the skin, the detector junction temperature will be close to that of the skin, so that this junction temperature will often provide a good reference measurement of local skin temperature. If a separate heater component is incorporated in the oximeter sensor, so as to deliver more heat to the patient's tissue than is delivered by the oximeter's own emitter (and hence to give greater enhancement of local perfusion), the temperature monitoring function of the detector diode will be especially valuable for providing measurements that may be used in controlling the heat delivered by the separate heater.

In one embodiment separate heater elements are provided to supplement heating by the emitter. Of particular value are the use of one or more such heater elements to deliver heat to the patient's tissue in areas away from the emitter, so that a larger area of tissue can be heated than by the emitter alone. Calibration of the emitter and/or detector diodes as temperature sensors, as described above, and incorporation of encoding means to communicate the temperature calibration(s) to the oximeter, provide an economical means of sensing the temperatures induced by the emitters and separate heaters.

Where exemplary circuits have been illustrated herein, the circuits have been of the "two-wire" type commonly used by the assignee of this invention, wherein red and infrared LEDs are connected "back to back", so that a drive current of one polarity activates the red LED and a current of the opposite polarity activates the infrared LED. The exemplary drive waveforms illustrated have been suitable for driving LEDs in this configuration. It will be clear to those skilled in the art that by straightforward adaptation of drive waveforms, the design principles of this invention can be applied to LEDs wired in any fashion, including particularly the common "three-wire" schemes, in which red and IR LEDs share one common wire, and a "four-wire" scheme in which the two LEDs are wired completely independently. The use of sensors incorporating more than two LEDs is also contemplated within the scope of the invention.

A potential clinical benefit of several of the sensor constructions described herein is that they provide a means of measuring local perfusion, because inherent in the design of these sensors is a capability to measure the local thermal resistance of a patient's skin, which is significantly affected by local blood flow. Devices which attempt to measure perfusion by measuring thermal resistance are known, and have not in the past been widely used, perhaps because of the difficulty of establishing a universally-applicable quantitative calibration relating thermal conductivity to perfusion. It has not previously been known to provide a perfusion monitor as an additional feature in an optical medical sensor, with little or no incremental sensor cost being required to add this function. Even lacking a universal quantitative calibration, such a sensor may be useful as a trend indicator for a particular patient, in which steadily reducing or increasing peripheral perfusion may be taken as one indicator of the patient's general welfare.

Another application of the sensor designs disclosed herein is the simultaneous measurement of oxygen saturation and the temperature of a bodily surface. In special circumstances, there may be clinical utility in knowing the skin temperature of a patient (for example, neonatal incubators are commonly controlled to maintain a patient's skin temperature at a set point close to 37° C.) It is also possible to apply pulse oximeter sensors to mucous membranes, such as the interior surface of a cheek or of the esophagus. Surface temperatures of mucous membranes are of special clinical interest because they often represent "core temperature," which is a primary vital sign. In particular, it would be possible to design a pulse oximeter sensor for use in the esophagus (such designs are known) with the additional feature of providing an esophageal temperature probe at little or no additional component cost.

Most of the specific application examples presented herein have been from the realm of pulse oximetry. It will be clear to those skilled in the art that similar strategies of temperature measurement and current control will be applicable to other optical medical sensors which place heat-dissipating elements in contact with a patient. Thus, for example, a multiple-LED optical sensor for non-invasive measurement of glucose concentration may benefit from the use of junction temperature sensing to ensure that the sensor does not burn a patient.

As will be understood by those of skill in the art, the present invention may be embodied in other specific forms without departing from the essential characteristics thereof. For example, a single resistor could encode both the temperature calibration value and the wavelength value of a red LED. Accordingly, the foregoing description is intended to be illustrative, but not limiting, of the scope of the invention which is set forth in the following claims.

What is claimed is:

1. A method for operating an optical medical sensor, comprising the steps of:

applying a driving current to a light emitter in said sensor, encoding in the sensor a forward voltage temperature characteristic of the light emitter, reading said encoded forward voltage temperature characteristic, measuring an electrical characteristic of said emitter which is indicative of its junction temperature, and modifying said driving current in accordance with said electrical characteristic and said encoded temperature characteristic to maintain the junction temperature of said emitter at or near a maximum value.

2. The method of claim 1 further comprising the steps of:

driving said light emitter with a known current;

measuring a resulting voltage across said light emitter; and adjusting said driving of said light emitter in accordance with a variance of said voltage from a desired voltage, the desired voltage being dependent on the encoded temperature characteristic.

3. The method of claim 2 wherein said measuring step is performed at a lower current than used in normal operation of said sensor.

4. The method of claim 1 wherein said step of modifying said driving current comprises the step of:

estimating a temperature at the skin of a patient based upon said maintained junction temperature; and modifying said driving current using said estimated skin temperature of said patient to maintain the temperature of the skin of said patient at or near a desired maximum value.

5. The method of claim 4 further comprising the steps of:

estimating a resistance of connections to said sensor from measured forward voltages; and providing an error signal if said resistance varies by more than a predetermined value.

6. The method of claim 1 further comprising the steps of:

using said encoded temperature characteristic to select a stored temperature calibration curve of said light emitter; and using said temperature calibration curve in a control system to limit the drive current for said light emitter to a safe value.

7. The method of claim 1 wherein said step of modifying said driving current comprises the steps of:

providing a table of encoded temperature characteristics and corresponding temperature responses for a junction temperature of said light emitter;

providing a maximum drive current for each temperature response, said maximum drive current being based on an assumed heat dissipation of said sensor and a maximum temperature at the skin of a patient.

8. The method of claim 7 further comprising the steps of:

providing in said sensor an encoding of a sensor type; and reading said encoded sensor type and selecting said assumed heat dissipation of said sensor based on said sensor type.

9. The method of claim 1 wherein said encoding step comprises a calibration process, applied during manufacture of said sensor, of:

placing said sensor in an environment at a first controlled temperature;

applying a predetermined current to said light emitter;

measuring a voltage across said light emitter; and incorporating in said sensor an encoding means to represent said voltage.

10. The method of claim 9 wherein said encoding means further contains information representing a rate of change of said voltage as a function of temperature.

11. The method of claim 1 wherein said optical medical sensor is provided as a pulse oximeter sensor.

12. A method for operating an optical medical sensor, comprising the steps of:

encoding a forward voltage temperature characteristic of an LED junction in said sensor;

reading said forward voltage temperature characteristic;

driving said LED with a known calibration current different from an operating current used in normal operation of said sensor;

measuring a forward voltage across said LED which is indicative of its junction temperature;

providing a table based upon the read forward voltage temperature characteristics, which table relates forward voltage to junction temperature of said light emitter;

determining a maximum drive current in accordance with said measured forward voltage and said table, the maximum drive current being based on an assumed heat spreading behavior of said sensor and a maximum temperature at the skin of a patient; and adjusting a driving of said LED in normal operation to be at or substantially at, but not to exceed, said maximum drive current.

13. An optical medical sensor system comprising:

a sensor including
a light emitter and
a coding element indicative of a forward voltage temperature characteristic of said light emitter; and a monitor including
a driver configured to provide a driving current to said light emitter,
a circuit configured to decode said coding element,
a reader configured to measure an electrical characteristic of said emitter which, together with the decoded element, is indicative of a junction temperature of the light emitter, and
a control circuit configured to modify said driving current of said light emitter in accordance with said coding element and said measured value of said electrical characteristic to maintain the junction temperature of the light emitter at or near a maximum value.

14. The optical medical sensor system of claim 13 wherein the control circuit is configured to estimate a temperature at the skin of a patient based upon said maintained junction temperature and to modify said driving current of said light emitter based upon said estimated skin temperature of said patient to maintain the temperature of the skin of said patient at or near a maximum value.

15. A method for evaluating an optical medical sensor, comprising the steps of:

measuring a voltage across a light emitting element in said sensor for a given drive current while maintaining a switch coupled in parallel with the light emitting element ON; and estimating a resistance of connections to said sensor from said measured voltage.

16. A method for evaluating an optical medical sensor, comprising the steps of:

providing drive current to a light emitter through first and second leads;

measuring a voltage across said light emitter in said sensor for a given drive current through third and fourth leads; and estimating a resistance of connections to said sensor from said measured voltage.

17. An optical medical sensor system comprising:

a sensor including
optical elements including a light emitter and a light detector;
a coding element indicative of a forward voltage temperature characteristic of one of said optical elements; and a monitor including
a driver configured to provide a driving current to said light emitter,
a circuit configured to read said coding element,
a reader configured to measure an electrical signal which is indicative of a junction temperature of said light emitter, and
a control circuit configured to modify said driving current of said light emitter in accordance with said coding element and said electrical signal to maintain the junction temperature of said light emitter at or near a maximum value.

18. The system of claim 17 wherein said maximum value of the junction temperature is based on an assumed heat dissipation of said sensor and a maximum temperature at the skin of a patient.

19. The system of claim 17 further comprising a heater element in said sensor.

20. An optical medical sensor system comprising:

a sensor including
a light emitter and a light detector; and a monitor including
a driver configured to provide a driving current to said light emitter,
a reader configured to determine a junction temperature of said light emitter and produce a junction temperature signal indicative of said junction temperature, and
a control circuit configured to modify said driving current of said light emitter in accordance with said junction temperature signal to maintain said junction temperature of said light emitter at or near a maximum value that is based on a maximum temperature at the skin of a patient.

21. The system of claim 20 wherein said monitor further includes a perfusion monitor configured to provide, in response to said junction temperature signal, a perfusion signal corresponding to blood perfusion of a portion of a patient where said sensor is connected.

22. The system of claim 20 wherein said monitor further includes:

a table of calibration coefficients; and
a selector configured to select a set of said calibration coefficients at least partially based on a value of said junction temperature signal.

23. The system of claim 20 wherein:

said sensor further includes a coding element indicative of a temperature characteristic of one of said optical elements;

said monitor further includes
a circuit configured to read said coding element, and
a control circuit configured to modify said junction temperature signal in accordance with said coding element.

* * * * *